United States Patent [19]

Rydell

[11] Patent Number: 5,007,908
[45] Date of Patent: Apr. 16, 1991

[54] ELECTROSURGICAL INSTRUMENT HAVING NEEDLE CUTTING ELECTRODE AND SPOT-COAG ELECTRODE

[75] Inventor: Mark A. Rydell, Golden Valley, Minn.

[73] Assignee: Everest Medical Corporation, Brooklyn Center, Minn.

[21] Appl. No.: 414,448

[22] Filed: Sep. 29, 1989

[51] Int. Cl.$^5$ .............................................. A61B 17/39
[52] U.S. Cl. ......................................... 606/47; 606/48; 606/50
[58] Field of Search ................................ 606/41, 45–50

[56] References Cited

U.S. PATENT DOCUMENTS

| | | | |
|---|---|---|---|
| 3,920,021 | 11/1975 | Hiltebrandt | 606/50 |
| 4,043,342 | 8/1977 | Morrison | 606/48 |
| 4,228,800 | 10/1980 | Degler et al. | 606/48 |
| 4,311,143 | 1/1982 | Komiya | 606/47 |
| 4,532,924 | 8/1985 | Auth et al. | 606/50 |
| 4,706,667 | 11/1987 | Roos | 606/48 |
| 4,919,131 | 4/1990 | Grossi et al. | 606/46 |

*Primary Examiner*—Max Hindenburg
*Attorney, Agent, or Firm*—Haugen and Nikolai

[57] ABSTRACT

An electrosurgical instrument for use in combination with an endoscope for cutting tissue and cauterizing-/coagulating the resulting wound area is described. The instrument comprises an elongated flexible tubular member having a proximal end, a distal end, and plural lumens extending therebetween. Affixed to the distal end of the tube is a bullet-shaped ceramic tip member having a centrally-disposed longitudinal bore passing through the side wall of the tip member. The ceramic exterior surface of the tip member is covered with a conductive layer forming a first inactive electrode. An electrical conductor joined to that electrode surface feeds back through a lumen of the tube to its proximal end where it may be coupled to an electrosurgical generator. Also running through a lumen in the tube is another conductor which can be made to project outwardly through the opening in the tip member. A hub having a spring-loaded plunger is affixed to the proximal end of the tube with the plunger joined to the wire so that when the plunger is depressed, the distal end of the wire will project a short distance beyond the extremity of the tip member. By coupling this second conductor to an electrosurgical generator, it becomes the active electrode of a bipolar pair.

8 Claims, 1 Drawing Sheet

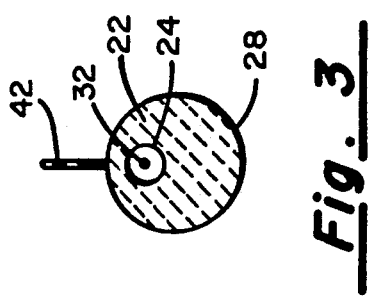
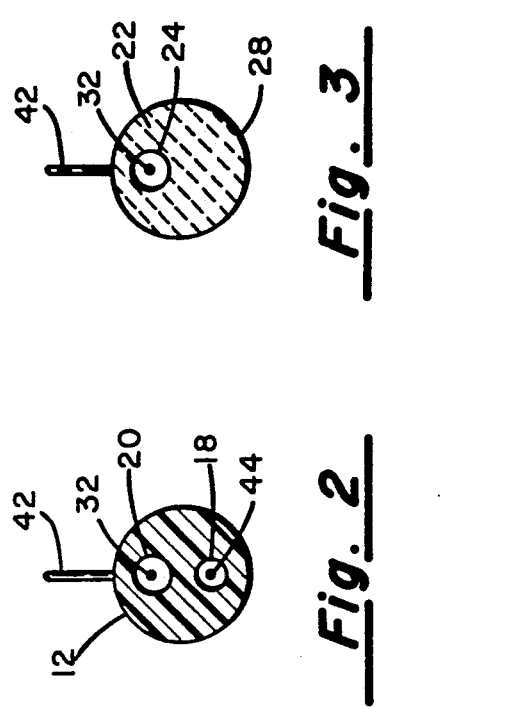
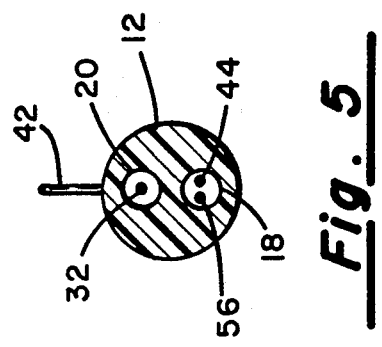
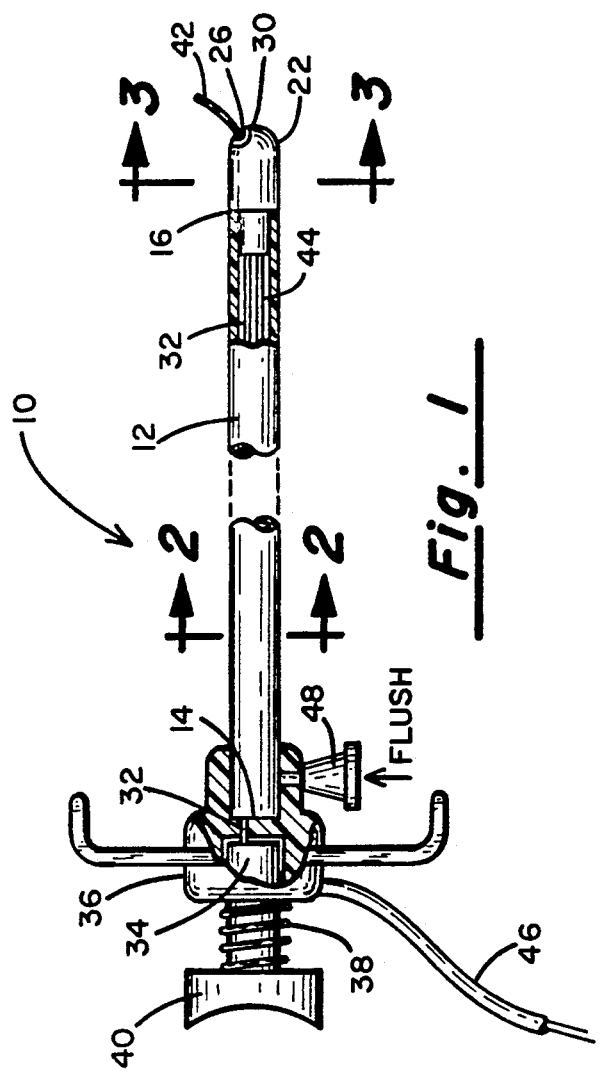
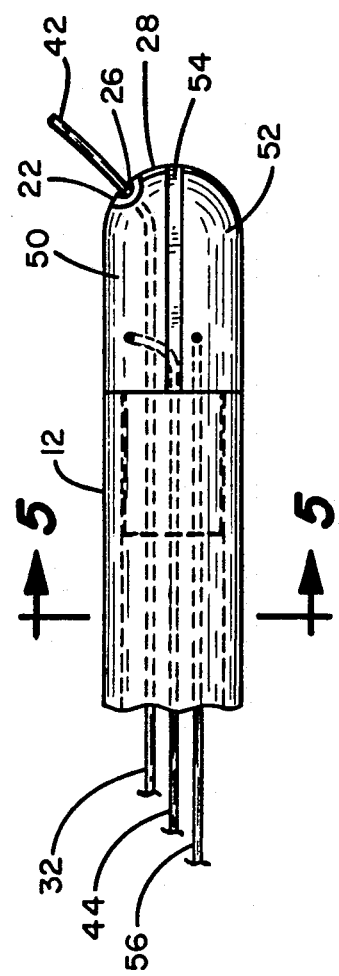

ELECTROSURGICAL INSTRUMENT HAVING NEEDLE CUTTING ELECTRODE AND SPOT-COAG ELECTRODE

BACKGROUND OF THE INVENTION

1. Field of the Invention

This invention relates generally to electrosurgical apparatus, and more particularly to a bipolar electrosurgical device useable with an endoscope for performing surgery in the gastrointestinal track.

2. Discussion of the Prior Art

In various surgical procedures carried out in the gastrointestinal track an endoscope may first be introduced through an appropriate body orifice and advanced until its distal end is disposed in the body cavity where the surgery is to take place. Typically, an endoscope will include a fiber-optic light pipe whereby the scene may be illuminated and viewed. A surgical instrument may then be introduced through the endoscope and used to cut or excise the tissue. For example, in cases where gall stones develop to a size where they are unable to pass through the duodenal papilla from the common bile duct, the opening of the papilla may be increased by surgically cutting the sphincter surrounding that opening.

The surgical removal of polyps from the colon may also be performed by passing an appropriate electrosurgical instrument through an endoscope. While a polypectomy snare is commonly employed in this application, smaller, less well developed polyps may be removed using an electrosurgical needle.

SUMMARY OF THE INVENTION

The present invention pertains to the design of an electrosurgical instrument having bipolar electrodes which may be passed through an endoscope where the bipolar electrodes of the instrument may then be deployed to effect both cutting and subsequent coagulation. In accordance with one aspect of the invention, the instrument may comprise an elongated, flexible, tubular member having a proximal end, a distal end and plural lumens extending between the proximal end and the distal end. Affixed to the distal end of the tube is a bullet-shaped ceramic tip having a centrally disposed longitudinal bore passing through the side wall thereof. The exterior surface of the ceramic tip is covered with a conductive layer forming a first, relatively large area electrode. An electrical conductor joined to that electrode surface feeds back through a lumen of the tube to its proximal end where it may be coupled to an electrosurgical generator. A second conductor also extends through a lumen in the elongated tubular member and means are provided for translating that second wire longitudinally so that its distal end can be made to project outwardly through the opening formed in the tip member. To facilitate the reciprocal displacement of the distal end of that wire relative to the opening formed in the metal coated ceramic tip, a hub having a spring-loaded plunger is affixed to the proximal end of the tube and the plunger is joined to the wire. A small gap exists between the metallized surface on the tip and the wire such that when the two are coupled to the electrosurgical generator and an appropriate RF voltage is applied, an arc is created at the wire elefctrode, with current flowing to the metalized ceramic return electrode with they are brought into contact with tissue to be severed.

In accordance with a further feature of the invention, the metallized surface on the ceramic bullet-shaped tip may be effectively divided by an insulating gap creating two rather than one electrode surfaces. During cutting, those two electrode surfaces would be connected in common to provide a single electrode cooperating with the reciprocally movable needle to create a bipolar pair where the surface area of the needle is substantially less than the surface area of the metallization on the ceramic tip. The instrument of the present invention may also be used to effect coagulation of blood and in this mode, the electrode segments formed on the ceramic tip are separately electrically connected to the coag output of the electrosurgical generator and used independently of the reciprocally deployable needle electrode.

Rather than having an elongated, flexible catheter-like tubular member, a relatively short rigid tube may be affixed to the plunger mechanism for use as an interoperative instrument.

DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

FIG. 1 is a partially sectioned side elevational view of the electrosurgical instrument in accordance with the present invention;

FIG. 2 is a cross-sectional view taken along the line 2—2 in FIG. 1;

FIG. 3 is a cross-sectional view taken along line 3—3 in FIG. 1;

FIG. 4 is a partial side elevational view of a further embodiment of the invention; and FIG. 5 is a cross-sectional view taken along the line 5—5 in FIG. 4.

DESCRIPTION OF THE PREFERRED EMBODIMENT

Referring first to FIG. 1, the electrosurgical instrument of the present invention is indicated generally by numeral 10 and is seen comprise an elongated, flexible plastic tubular member 12 having a proximal end 14 and a distal end 16. The cross-sectional view of FIG. 2 reveals that the tube 12 includes a first lumen 18 and a second lumen 20. The tube may be extruded so as to possess two lumens or, alternatively, two separate lumens may also be formed by running a second, smaller diameter tube through a single lumen of a first tube.

Affixed to the distal end 16 of the tubular member 12 is a smoothly rounded, bullet-shaped ceramic member 22 which includes a longitudinal bore 24 formed completely therethrough to define an aperture 26 at the surface of the ceramic tip member 22. The ceramic employed may be aluminum nitride or aluminum oxide but limitation to these two candidates is not intended.

Plated, sprayed, dipped, screened or otherwise formed on the exterior surface of the ceramic tip 22 is a conductive layer 28 of an appropriate metal, such as silver or nickel which is biocompatible and non-toxic. The metal is removed around the perimeter of the aperture 26 to define a gap 30 of a predetermined dimension, the purpose of which will be explained in greater detail below.

A first conductor 32 extends through the lumen 20 and through the bore 24 formed in the ceramic tip. The proximal end of the conductor 32 is mechanically attached to the proximal end of a plunger 34 which is fitted into a bore formed in a molded plastic hub 36 secured to the proximal end 14 of the elongated flexible tubular body 12. A return spring 38 surrounds the plunger shaft 34 and cooperates with the hub 36 and a thumb rest 40 to normally urge the plunger in the proximal direction. Depression of the plunger 34 against the force of the spring causes the distal end 42 of the conductor 32 to project out through the opening 26 formed in the ceramic tip member 22. Subsequent release of the plunger results in the proximal end portion 42 of the wire 32 retracting back within the interior of the tip 22.

As is further shown in FIG. 2, a second conductor 44 extends through its lumen 18 and the distal end of the wire 44 connects to the metallization layer 28 formed on the ceramic tip. The instrument 10 is adapted to be connected by an electrical lead 46 and to the output terminals of an electrosurgical generator such as of the type described in the Stasz patent application Ser. No. 07/254,203, filed Oct. 6, 1988, and assigned to applicant's assignee. The wires in lead 46 are electrically connected within the molded housing 36 to the conductors 32 and 44.

The surgical field viewed through the endoscope may be flushed free of blood and other body fluids by introducing an appropriate flush solution through the Luer fitting 48 which leads to the lumen 20 formed in the catheter body 12.

In use, the instrument 10 may have the tubular body portion 12 routed through an endoscope to a location within the body where electrosurgery is to be performed. Once the distal tip 22 has approached the site, the surgeon may depress the thumb rest 40 to cause the distal end portion 42 of the conductor 32 to project out through the aperture 26. Now, by actuating the "cut" foot pedal associated with the electrosurgical generator, a RF voltage is developed between the projecting portion 42 of the wire 32 and the metallization 28 covering the ceramic tip 22. Because of the substantial difference in electrode area between the projecting wire 42 and the metallization 22, the portion 42 assumes the role of the active bipolar electrode while the metallization 22 comprises the return electrode. When the two electrodes are brought into contact with tissue to be cut, an electric arc is created between the active electrode and tissue, and flowing to the return electrode with the arc causing the tissue to be severed. Simultaneously, a saline or other suitable solution may be injected through the Luer fitting 48 and through the lumen 20 to exit the distal port 26 to wash the site facilitating the viewing through the endoscope of the surgical field.

The principles of the present invention may also be applied to a hand-held interoperative electrosurgical instrument wherein the tubular member 12 is relatively short and inflexible. Otherwise, the structural features remain as previously described. This latter instrument may be employed to cut tissue and later coagulate blood at the site of the surgery. Rather than being manipulated through an endoscope, the instrument, so modified would be used much like an electrosurgical scalpel of the type having a rigid handle and a distally positioned blade carrying the requisite electrode surfaces.

FIGS. 4 and 5 illustrate an alternative embodiment of the present invention adding coagulation as a feature. The device of FIG. 4 differs from that of FIG. 1 primarily in the distal tip metallization pattern. Rather than having a uniform coating of metallization on the distal tip, in the arrangement of FIG. 4, the metallization is effectively divided into two segments of relatively equal area 50 and 52 separated by a insulating gap 54. The conductor 44 connects to one of the two segments and a further conductor 56 extends through the lumen 18 to connect to the other metallized segment. The conductor 56 leads back to the proximal hub 36 where it joins to a further conductor in the cable 46 leading to the electrosurgical generator (not shown).

When the instrument of FIGS. 4 and 5 is to be used in a "cut" mode, the distal end portion 42 of the conductor 32 is made to project out through the aperture 26 and cooperates with the metallization segments 50 and 52 which at this time are connected in common. When the instrument is to be used for coagulating blood and other tissue, the plunger is released such that the return spring 38 pushes the plunger in the proximal direction, withdrawing the distal end portion 42 of the conductor 32 back within the bore formed in the ceramic tip member 22. When operating in the coag mode, the conductors 44 and 56 are no longer electrically connected in common at the electrosurgical generator, but instead, are separately energized by the RF power from the generator and the metallization segments 50 and 52 then comprise a bipolar coagulating electrode pair.

It should be readily apparent to those skilled in the art that with conductors 44 and 56 extending through the same lumen 18, it is necessary that they be insulated from one another over their length. If uninsulated wire is to be utilized, a further lumen may be provided in the tube member 12 to maintain the conductors 44 and 56 isolated from one another.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical instrument comprising:
   (a) an elongated tubular member having a proximal end, a distal end and plural lumens extending between said proximal and distal ends;
   (b) a bullet-shaped ceramic tip member affixed to said distal end of said tubular member, said tip member having a longitudinal bore formed therein, said bore exiting through an opening in the exterior of said tip member at a location displaced laterally from the longitudinal axis of said tubular member;
   (c) a first conductor disposed in one of said lumens;
   (d) means connected to said proximal end of said tubular member and joined to said first conductor for selectively displacing said first conductor whereby the distal end of said first conductor may be made to pass through said longitudinal bore and said opening;

(e) a conductive surface adhered to said exterior of said ceramic tip member and surrounding but spaced from said opening; and (f) a second conductor passing through another of said plural lumens and electrically joined to said conductive surface.

2. The electrosurgical instrument as in claim 1 wherein said conductive surface includes first and second segments insulatively spaced from one another on said tip member.

3. The electrosurgical instrument as in claim 2 and further including a third conductor extending through said another of said plural lumens and electrically joined to the one of said first and second segments not joined to said second conductor.

4. The electrosurgical instrument as in any of claims 1-3 wherein the ceramic is selected from a group including aluminum oxide and aluminum nitride and said conductive surface is silver.

5. The electrosurgical instrument as in claim 1 and further including means for coupling said first and second conductors to an RF voltage such that an arc is created between the portion of said first conductor extending outward through said opening and said conductive surface when said portion of said first conductor and said surface are brought into contact with body tissue.

6. The electrosurgical instrument as in claim 3 and further including means for coupling said second and third conductors to said RF voltage for coagulating body fluids.

7. The electrosurgical instrument as in claim 1 wherein said means connected to said proximal end of said tubular member comprised a hub having a spring-loaded plunger passing through said hub, said plunger being coupled to said first conductor.

8. The electrostatic instrument as in claim 3 wherein said second and third conductors are connected in common with one another when said first conductor is connected to an RF voltage source.

* * * * *